US009439807B2

(12) United States Patent
Koplin

(10) Patent No.: US 9,439,807 B2
(45) Date of Patent: *Sep. 13, 2016

(54) APPARATUS AND METHOD FOR PERFORMING PHACOEMULSIFICATION

(71) Applicant: FLUIDICS PARTNERS, LLC, New York, NY (US)

(72) Inventor: Richard S. Koplin, New York, NY (US)

(73) Assignee: FLUIDICS PARTNERS, LLC, New York, NY (US)

( * ) Notice: Subject to any disclaimer, the term of this patent is extended or adjusted under 35 U.S.C. 154(b) by 54 days.

This patent is subject to a terminal disclaimer.

(21) Appl. No.: 14/197,295

(22) Filed: Mar. 5, 2014

(65) Prior Publication Data
US 2014/0276365 A1 Sep. 18, 2014

Related U.S. Application Data

(63) Continuation-in-part of application No. 13/625,158, filed on Sep. 24, 2012, now abandoned.

(60) Provisional application No. 61/773,998, filed on Mar. 7, 2013, provisional application No. 61/539,016, filed on Sep. 26, 2011, provisional application No. 61/570,555, filed on Dec. 14, 2011.

(51) Int. Cl.
A61F 9/007 (2006.01)
A61M 1/00 (2006.01)
A61B 17/32 (2006.01)

(52) U.S. Cl.
CPC ... *A61F 9/00745* (2013.01); *A61B 17/320068* (2013.01); *A61F 9/00763* (2013.01);
(Continued)

(58) Field of Classification Search
CPC ........... A61F 9/00736; A61F 9/00745; A61F 9/00754; A61B 2017/320072; A61B 2017/320076; A61B 2017/320084; A61B 2017/320088; A61M 1/0084; A61M 1/0058
USPC ........................................... 606/107; 604/22
See application file for complete search history.

(56) References Cited

U.S. PATENT DOCUMENTS 5,188,589 A 2/1993 Wypych et al.
5,242,385 A 9/1993 Strukel
(Continued)

FOREIGN PATENT DOCUMENTS

JP 2007289700 8/2007

OTHER PUBLICATIONS

Inter V, Quadra Fuse, "Multi-Pronged Injection, Gainesville", Florida, Jul. 2005.
(Continued)

*Primary Examiner* — Eric Rosen
*Assistant Examiner* — George J Ulsh
(74) *Attorney, Agent, or Firm* — Gottlieb, Rackman & Reisman P.C.

(57) ABSTRACT

An apparatus provides mechanical energy to vibrate a tip. The tip preferably formed of multiple prongs positioned approximately circumferentially (either symmetrically or asymmetrically) around an orifice of a needle. The tip is designed to emulsify a cataractous lens and to collect the resulting detritus through an aspiration aperture. An irrigating sleeve whose apertures/ports are protected from relative occlusion by untoward excursions of the phaco needle by a system of elevated stabilizing devices rising from within the inner wall of the sleeve (or from the outer wall of the phaco needle); this results in a plume or river of irrigating fluid exiting the sleeve that mitigates untoward dispersion of infusion fluid and material caught in its path including lens detritus, iris and other anatomical structures. This also provides for a more efficient process at the needle tip and therefore enhances aspirations of lens detritus in a more efficient and salutary manner as it flows to the aspiration aperture, said plume extend around the prongs. The prongs can be driven at either subsonic frequencies or ultrasonic frequencies. A stabilizer is provided to prevent the needle from interfering with the flow of the irrigating fluid during operation.

12 Claims, 8 Drawing Sheets

(52) U.S. Cl.
CPC . *A61M1/0058* (2013.01); *A61B 2017/320072* (2013.01); *A61B 2017/320084* (2013.01); *A61B 2017/320088* (2013.01)

(56) References Cited

U.S. PATENT DOCUMENTS

| | | | |
|---|---|---|---|
| 5,354,265 | A | 10/1994 | Mackool |
| 5,464,389 | A | 11/1995 | Stahl |
| 5,718,676 | A | 2/1998 | Barrett |
| 5,725,495 | A | 3/1998 | Strukel et al. |
| 5,741,226 | A | 4/1998 | Strukel et al. |
| 5,941,887 | A | 8/1999 | Steen et al. |
| 5,989,209 | A | 11/1999 | Barrett |
| 6,234,993 | B1 | 5/2001 | Terpilowski et al. |
| 6,299,617 | B1 | 10/2001 | Stamler |
| 7,204,820 | B2 | 4/2007 | Akahoshi |
| 2009/0093750 | A1* | 4/2009 | Herman ............... A61F 9/00745 604/22 |
| 2009/0099536 | A1 | 4/2009 | Akahoshi |
| 2009/0137971 | A1 | 5/2009 | Akahoshi |
| 2009/0137992 | A1 | 5/2009 | Nallakrishnan |
| 2011/0172590 | A1 | 7/2011 | Akahoshi |

OTHER PUBLICATIONS

Howard Instruments, "Products Focused on the Total Eye", Tuscaloosa, Alabama, May 1, 1998.

EyeCare/Tumble, "How to Help Prevent Cataracts" . . . Oct. 27, 2011.

\* cited by examiner

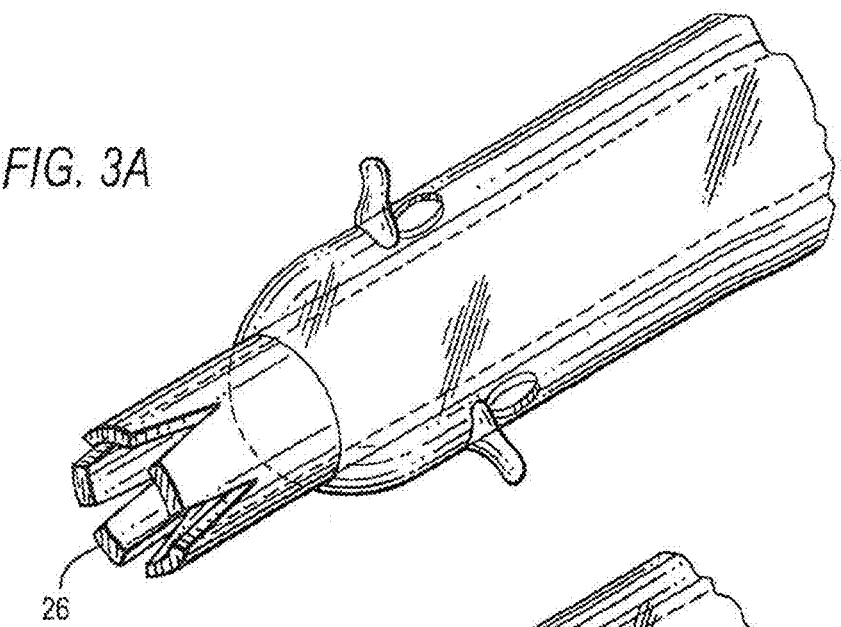
FIG. 3A
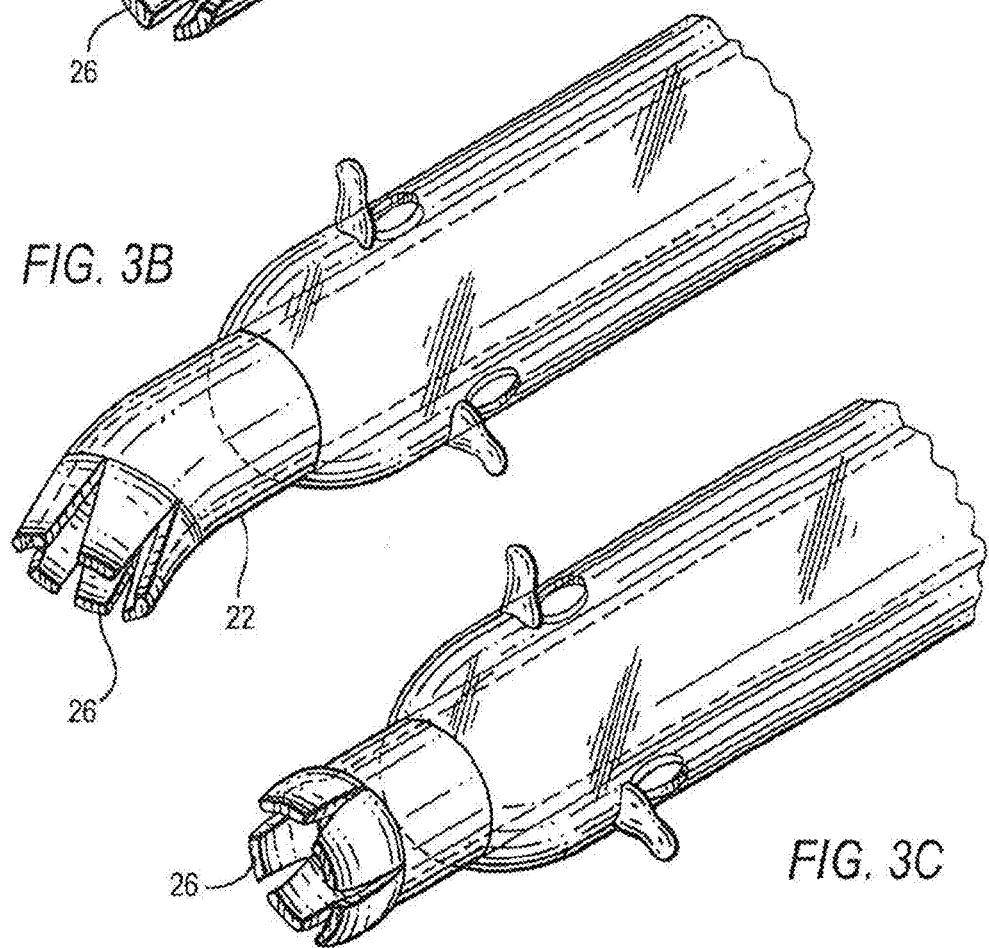
FIG. 3B
FIG. 3C

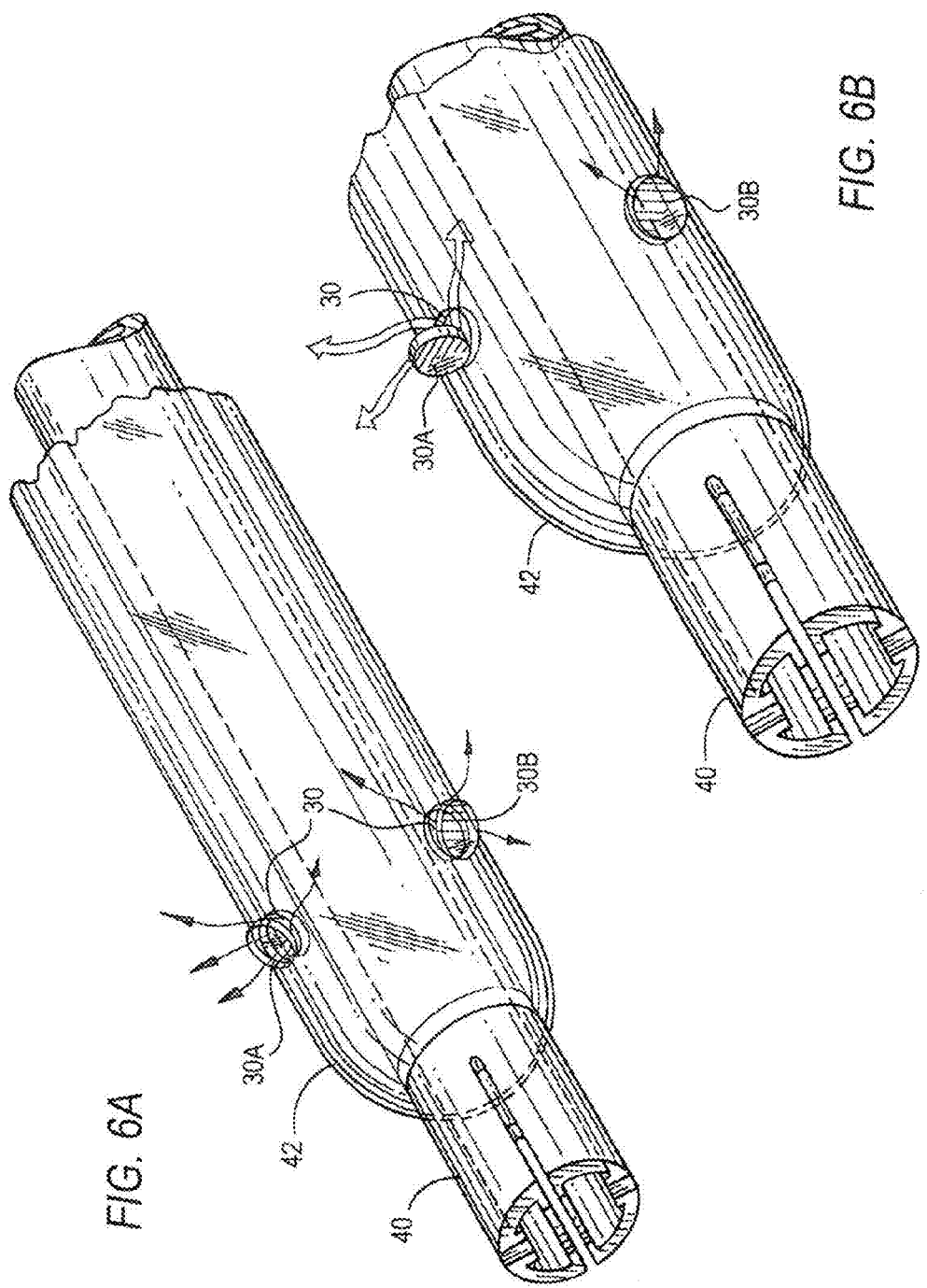

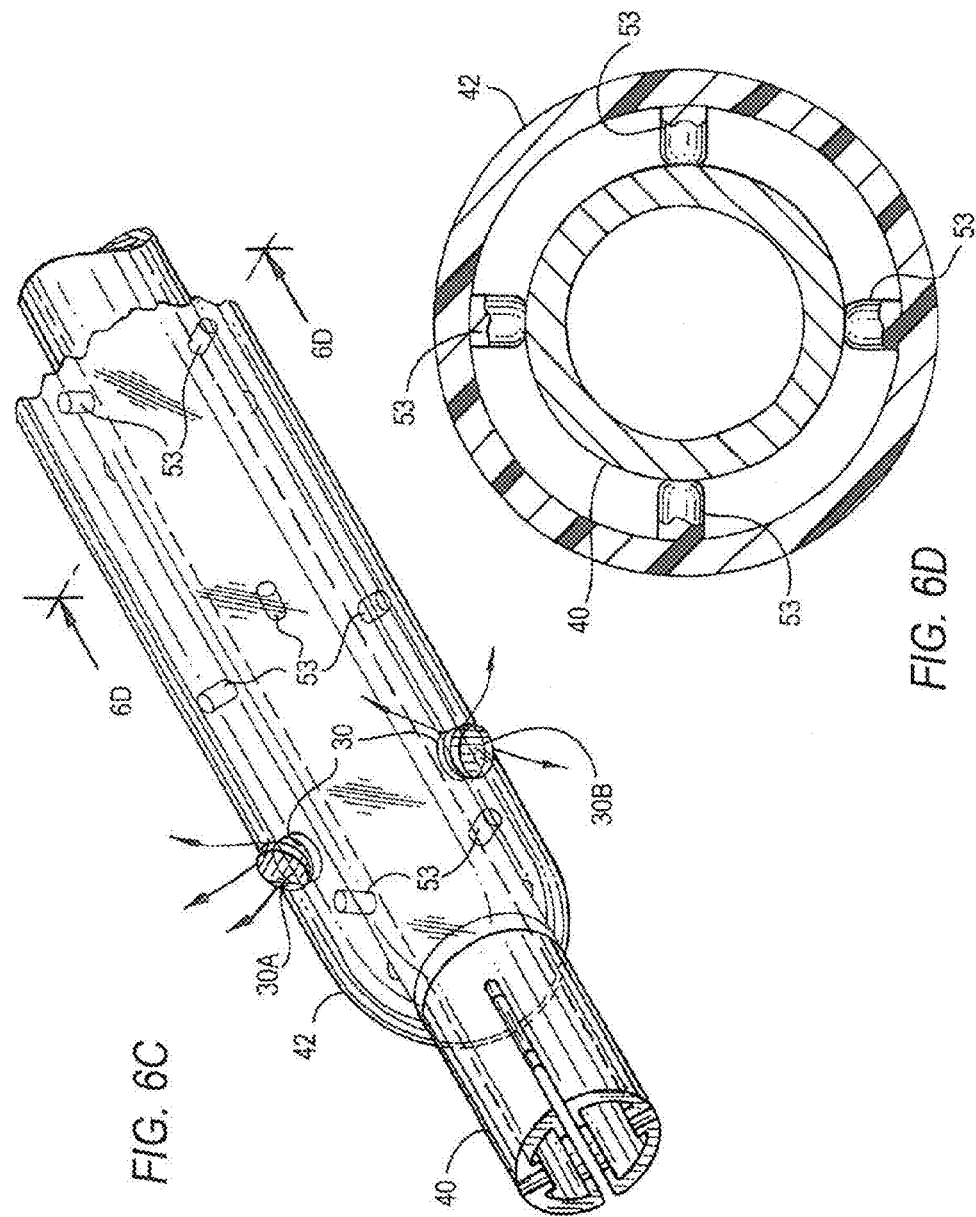

APPARATUS AND METHOD FOR PERFORMING PHACOEMULSIFICATION

RELATED APPLICATIONS

This application claims priority to U.S. Provisional Application Ser. No. 61/773,998 filed on Mar. 7, 2013 and is a continuation in part of U.S. application Ser. No. 13/625,158 filed Sep. 24, 2012 now abandoned claiming priority to U.S. Provisional application Ser. No. 61/539,016 filed Sep. 26, 2011; and Ser. No. 61/570,555 filed Dec. 14, 2011, all incorporated herein by reference in their entirety.

BACKGROUND OF THE INVENTION

A. Field of Invention

This invention pertains to an apparatus for performing phacoemulsification and fluid infusion and maintenance within the eye. The apparatus includes a sleeve with lateral outlets or ports for ejecting fluid into the eye in a predetermined pattern selected to prevent detritus resulting from the phacoemulsification to migrate away from the site and, possibly into the eye. The apparatus may also include a needle having a tip with several prongs directing sonic waves at the site of interest. The apparatus includes stabilizers incorporated within a silicone (or other pliant material) sleeve surrounding and maintaining the phacoemulsification needle in a stable, relatively central position within the sleeve, (Alternatively the stabilizers may be attached to the outer wall of the needle.) The stabilization of the needle relative to the infusion ports associated with the distal portion of the sleeve is intended to "normalize" flow from the sleeve and into the eye, and thereby mitigating the impact of sudden and forceful infusion flow against various anatomical elements within the eye, B. Description of the Prior Art Phacoemulsification is a procedure used to break up and remove the natural lens from the capsular bag within the eye of a person. Most often the procedure is used as a means of treating a person having cataracts. The procedure involves making a small incision in the eye and introducing a thin needle formed on a horn through the incision. The horn is coupled to an ultrasonic generator that vibrates the needle in a predetermined ultrasonic frequency range causing the natural lens to fragment and become emulsate. The nuclear emulsate within capsular bag is aspirated during this process and simultaneously irrigation (infusion) produces a stabilizing effect in the anterior and posterior chambers, keeping the eye inflated.

To complete the operation an intraocular lens implant is then inserted into the capsular bag (usually through the same incision incorporating the ultrasonic handpiece).

While the technology has for the most part been broadly accepted as the community norm presently available equipment is noted to have several disadvantages. One these disadvantages is that in a typical equipment for performing phacoemulsification, the infusion (delivered by the surrounding sleeve) and aspiration functions (via the central bore of the phacoemulsification needle) are inherently in close proximity. Due to the unfettered ability for the phaco needle to make wide excursions within the surrounding infusion sleeve, under certain conditions the infusion fluid stream within the eye may interact in a deleterious manner tending to drive lens detritus away from the aspiration flow. Because of this phenomenon the phacoemulsification process is not only inherently less efficient but nuclear or other lens material may be driven far afield of the hand-piece, become lost to the surgical field, and at times remain in the eye in various hidden anatomical locations. Additionally fluid, forcefully entering the eye via the ports adjacent to the tip of the phaco needle tends impact on the iris under certain conditions as well as driving fluid into the back if the eye, inviting a form of intraocular glaucoma known as misdirected aqueous.

Another disadvantage of the existing apparatus is that the ultrasonic generator and the needle being vibrated has a tendency to generate excessive heat and must be cooled by infusion fluid to insure that the heat thus generated does not cause any internal injuries in the eye. A further disadvantage of existing phacoemulsification apparatus is that the needle ends in a ring-shaped end that is not a very effective emitter of ultrasonic sound waves and therefore the apparatus ultrasonic waves of relatively large amplitudes.

SUMMARY OF THE INVENTION

The present invention provides an apparatus that overcomes, or at least alleviates the disadvantages discussed above. An apparatus for removing the natural or crystalline lens (usually with cataracts) from a patient's eye includes a hand-held body with horn-shaped portion terminating in a needle. The horn-shaped portion provides mechanical energy for breaking up the natural lens.

An appropriate irrigating fluid (typically a salient aqueous solution) is provided through the handle and flows along the outside of the needle, within the (silicone) sleeve) and exits through one or more lateral opening (known as ports) into the anterior portion of the eye. The lens detritus resulting from the emulsification process is aspirated through a central orifice in the needle tip. The tip is fabricated of a metallic material (titanium is customary but could be other suitable metal). A transducer acts as a sound generator and generates ultrasonic or sub-sonic sound waves that drive and vibrate the tip of the needle.

As previously mentioned, the hand piece is coupled to a suitable vibrating mechanism that vibrates the tip of the needle. The conventional practice until now has been to apply sound waves at an ultra-sonic range (typically 30-60 KHz) and normally do not contact the natural lens.

However the present inventor has found that, alternatively, the needle can be driven within the normal sonic range (typically 40-400 Hz). In this embodiment, the prongs preferably contact the lens nucleus and epinucleus and their vibration through both mechanical means and ultrasonic cavitation causes the lens to break up and form an emulsate.

The needle is preferably made of titanium and is attached to the horn. The needle is formed of a plurality of prongs arranged in a circumferential symmetrically or asymmetrically configuration defining the tip of the needle about an aspiration orifice.

In one embodiment it has between two and five (or more) prongs that extend either in parallel with the needle axis or may be bent to as much 15-20 degrees toward the center of needle and its orifice. The prongs may be rounded at their ends to provide a potentially salutary effect on the capsule if they engage the capsule inadvertently.

Depending on the configuration selected, the apparatus provides a number of advantages to the present state of the art:

1. The low frequency embodiment requires no coolant since no heat is generated. In the high frequency embodiment, less coolant may be required.

2. Visibility using a multiple pronged-needle fragmenting system may be enhanced making the risk of misjudging emulsification depth less likely.
3. An apparatus with a multi-pronged tip uses the cumulative effect of the energy delivered through the prongs to the fragmentation process; in association with the re-directed fluidics described herein which this may make for an efficient and less chaotic process at the needle tip. The needle prongs may be angled to increase efficient cutting.
4. Tips may be energized to act in transverse, oscillatory longitudinal or rotational modes.
5. The lateral flow of the irrigating fluid from the needle results in a more efficient procedure with less repulsion of lens material away from the cutting process and towards the posterior section of the eye.
6. The needle terminating in the tips is stabilized within the sleeve thereby eliminating or reducing the relative movement between the needle and the sleeve.
7. Stabilizing the needle within the sleeve further insures that orifices in the sleeve near the tip do not blocked by the needle and therefore the fluid from the sleeve is free to flow outwardly, preferably in a predetermined plume or other shape.

BRIEF DESCRIPTION OF THE DRAWINGS

FIGS. 3A, 3B and 3C show various alternate configurations for the needle of FIG. 1 and its prongs;

FIG. 6A shows a somewhat diagrammatic side view of a needle tip without stabilization;

FIG. 6B shows the needle of FIG. 6A being deflected during a procedure and its effect on the fluid flow in the sleeve;

FIG. 6C shows a modified needle tip with stabilizers to prevent needle deflection; and FIG. 6D shows a cross sectional view of the needle tip of FIG. 6C.

DETAILED DESCRIPTION OF THE PREFERRED EMBODIMENT

Figure 1:
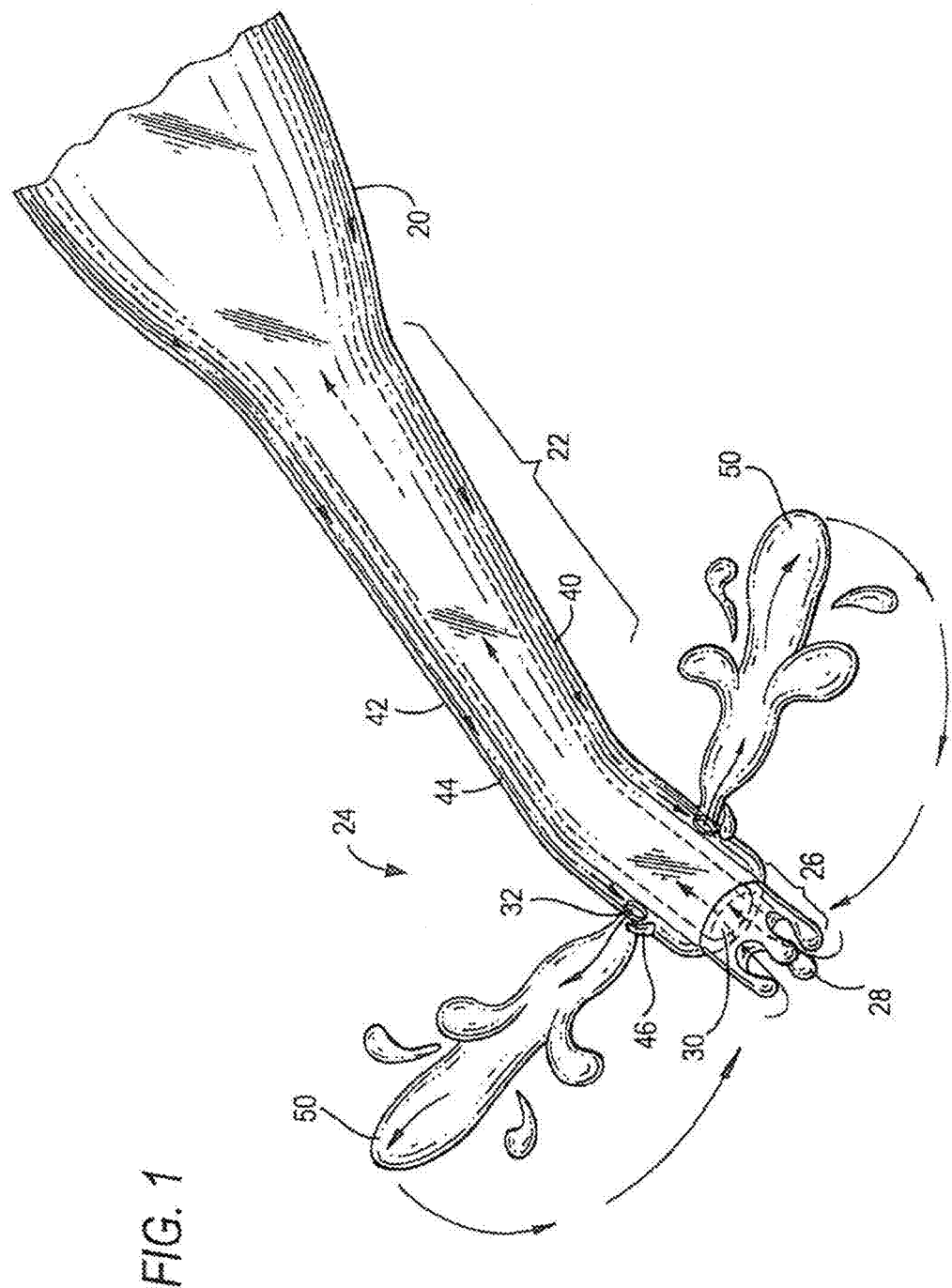
FIG. 1 shows an enlarged side orthogonal sectional view of the needle tip for one embodiment of the apparatus of FIG. 1A.
Figure 1A:
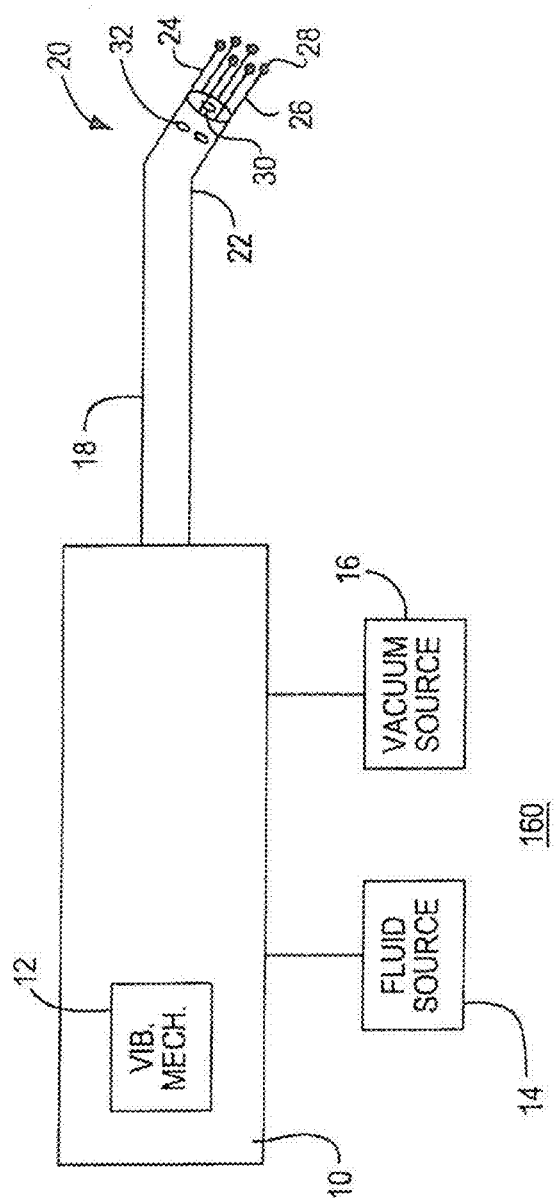
FIG. 1A shows a block diagram of an apparatus constructed in accordance with this invention.

Referring first to FIG. 1A, an apparatus 100 constructed in accordance with this invention includes a handle 10 that includes a vibrating mechanism 12 and is connected to a fluid source 14 that provides irrigating fluid and a vacuum source 16. One end of the handle 10 is provided with a horn 18 terminating with a needle 20. The needle 20 is preferably bent, as at 22. The needle 20 includes a tip 24. In one embodiment, the tip 24 is formed of a plurality of prongs 26 extending generally coaxially along needle 20. The prongs 26 are terminated in one embodiment with crowns 28. The prongs 26 are disposed circumferentially around a central aspiration aperture 30. Tip 24 further includes a plurality of irrigation apertures 32.

The vibrating mechanism 12 may be, for example, a transducer that provides excitation for the mechanical vibration of the tip 24 (at either a sonic, e.g. 40-400 Hz or ultrasonic, e.g. 30-60 KHz, frequency range) to cause the natural lens in the capsular bag of an eye (not shown) to break up, as discussed in more detail below. This vibration is transmitted to prongs (described in more detail below) through a metal tube and these elements cooperate to cause the prongs to move in at least one of a translational motion, rotational motion, etc.

The horn 18 is typically a housing incorporating an integrated metal tube which tapers to fit the casing as it approaches the cut-outs that represent the emulsifying needle prongs. The needle prongs are attached to the horn assembly and are disposable. In one embodiment, the needle prongs could be sectioned elements of the integrated tube attached to the horn or independent metallic materials designed for this purpose.

As shown in FIG. 1, the tip 24 includes a central tube 40 (typically made of titanium) preferably made of a metallic or other similar relatively stiff material. The tube 40 is surrounded by a sleeve 42. The sleeve is often manufactured of silicone but may be of other materials, and is provided with either an annular cannula 44 or one or more tubular longitudinal openings extending from the handle to the irrigation apertures 32. The sleeve is attached tightly around the central tube 40 past the irrigation apertures 32.

As mentioned above, preferably the tip 24 is formed of a plurality of prongs 26 having crowns 28. The vibrating mechanism 12 and tube 40 cooperate to cause the prongs 26 to vibrate in one of a series of controlled motions. The optimal efficiency mode of vibration of these prongs is dependent on the length, thickness and material of the prongs, the size and weight of the crowns 28 and the angle of the prongs 26 with respect to the longitudinal axis of the tube 40. The multiple pronged tip is configured and arranged to increase the efficiency of emulsification (as compared to previous devices) through contact to lens material.

The apparatus is used as follows. A small opening is first made in the capsular bag of the eye. The lens is either engaged within the capsular bag or the lens is dislocated anteriorly. Either way in the next steps, the tip 24 of the needle 20 is made to have contact with the nucleus of the lens. This step is facilitated by the bent 22 formed in the needle.

Next, the vibrating mechanism is started coincidentally with the infusion of irrigating fluid 50 which is introduced through the cannula 44.

Preferably the irrigation apertures 32 are covered or closed by flexible baffles or other designs meant to redirect fluid to a more lateral of tangential direction 46 so the sleeve 42 (made, for example, from silicone) presents a substantially continuous outer surface as the needle 20 is juxtaposed or in contact to the lens nucleus. However, once the tip 24 has engaged the nuclear lens material either outside or within the capsular bag, irrigation fluid usually under the force of gravity from source fluid 14 through the cannula 44. The fluid pushes the baffles 46 open and then exits into the eye forming a plume 50 that extends at an angle away from the prongs 26 forming an angle of 90 degrees or more or less with the longitudinal axis of tube 40. As the prongs 26 vibrate, the natural or crystalline lens of the eye is broken up and emulsified. The central aperture 30 is connected through central tube 40 to the vacuum source 16 causing fluid and emulsate to flow through the central aperture 30 and out the eye to the machine console. Using the invention and its redirected infusion apertures 32, the lens nuclear fragments are readily emulsified by the vibrating prongs 26 and detritus is more efficiently removed from the eye and is less likely to be lost to aspiration and left in the eye.

In prior art devices, irrigation fluid exits between or close to the prongs (for cooling the prongs) and is directed axially along the prongs forming a fluid flow in direction X in FIG. 1. Detritus formed at or by the prongs is caught up in this flow and is carried away from the tip into remote zones often beyond the capsular bag and to other parts of the eye. As a result of the inefficiencies of prior art emulsification of nuclear lens may take longer, and in some cases the removal may be incomplete, especially when the detritus reaches other parts of the eye. In the present invention, instead a toroidal flow Y is established that is salutary to the aspiration functions of the device and since it is less repulsive to fragmenting lens material will allow for greater efficiency of ultrasonic or subsonic emulsification. Therefore detritus is more directly aspirated towards the aperture 30 and not towards remote areas of the eye. As a result, the detritus is removed more efficiently and/or faster than in prior art devices.

For the low frequency embodiment, the configurations shown are even more advantageous because fluid is not required to cool the prongs, since at such frequencies, and without significant cavitation, damaging heat is not produced.

Figure 2:
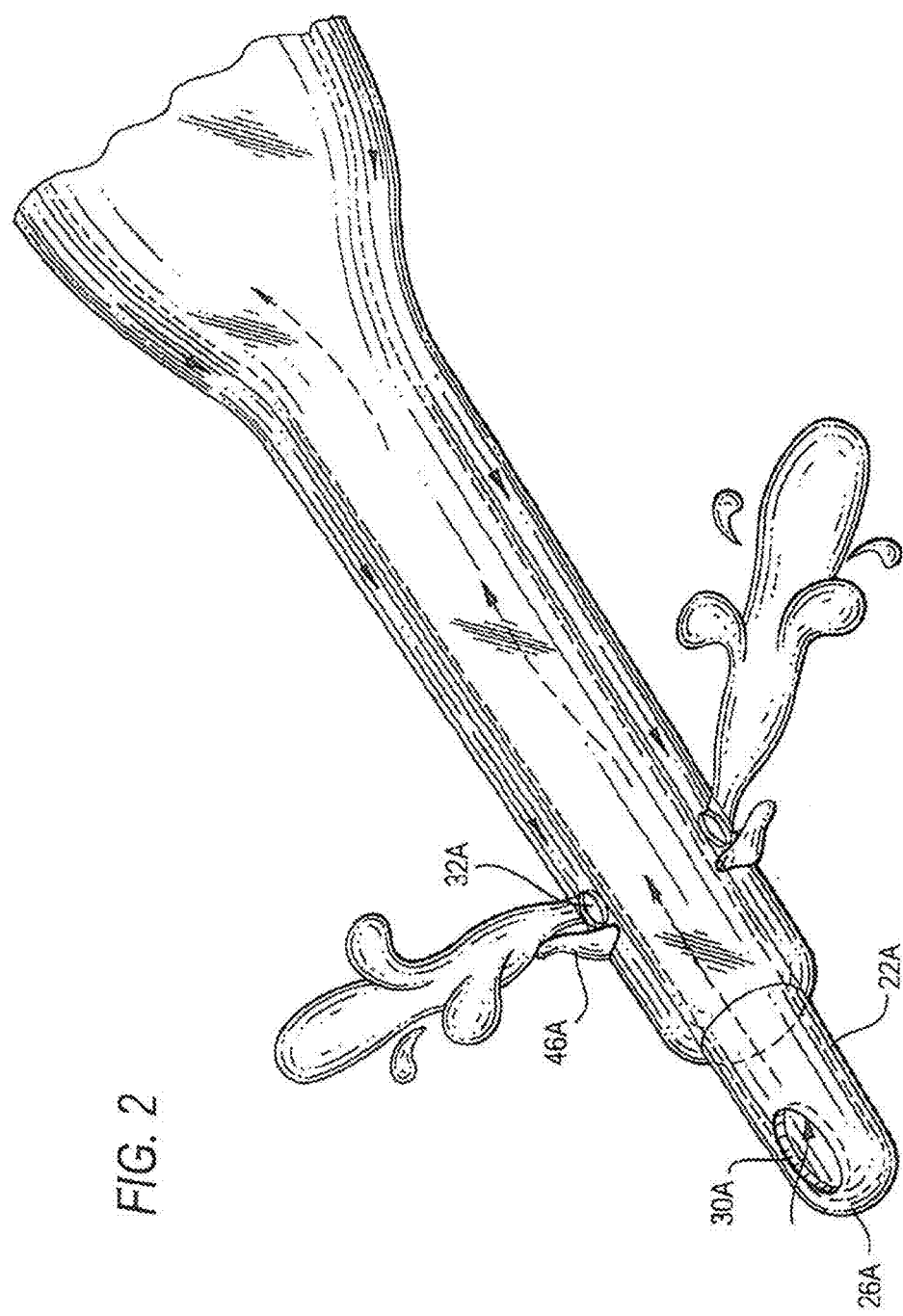
FIG. 2 shows an enlarged orthogonal section of an alternate embodiment of the invention.
Figure 2A:
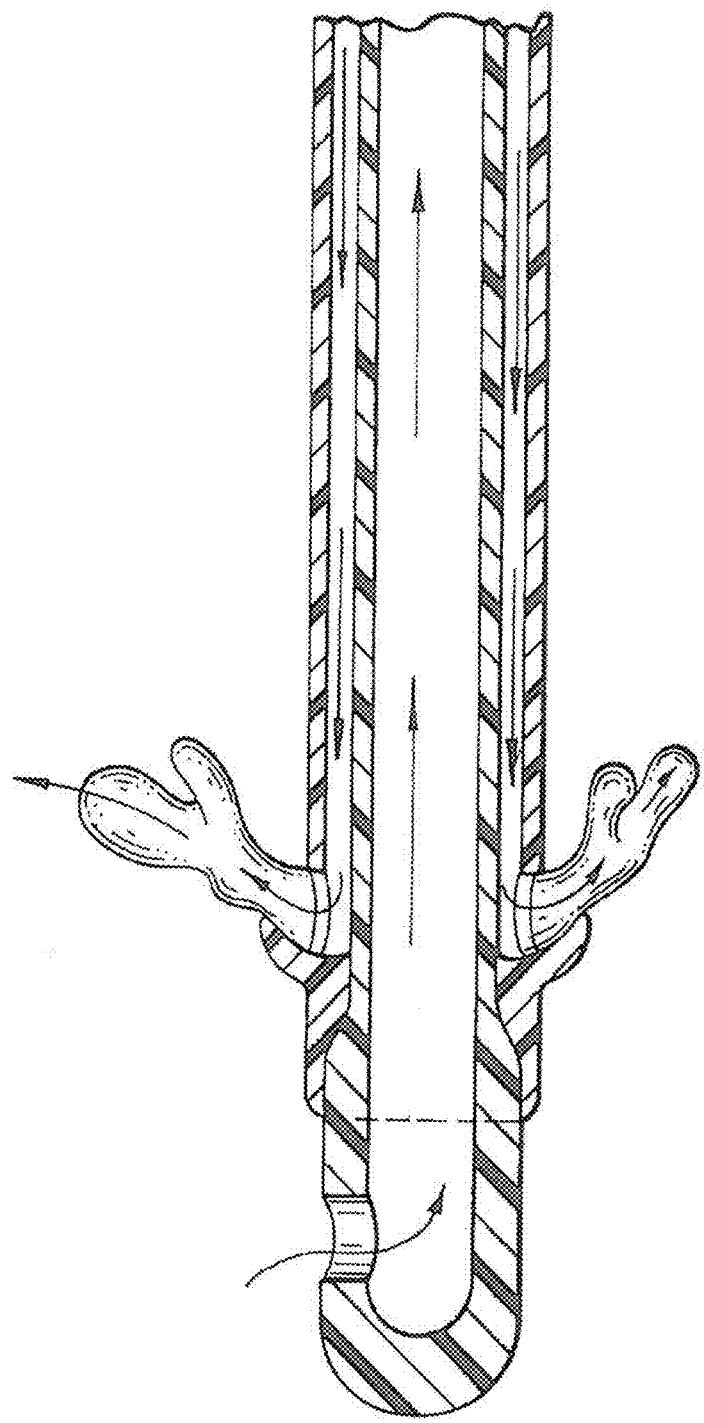
FIG. 2A shows a side sectional view of the embodiment of FIG. 2.

In one embodiment shown in FIG. 2, the tip 24A is somewhat bullet shaped with a round nose 26A rather than several prongs. Excitation for breaking up the lens is provided at the nose 26A. In this embodiment, irrigation fluid is still provided through several apertures 32A (with flaps 46A) at a position axially recessed from the tip 22A. The fluid then picks up the detritus and is vacuum out from the capsular bag through the aperture 30A.

The prongs and the needle 20 can be arranged into several configurations. In FIG. 1 the needle is provided with bend 20 and the prongs 26 are disposed generally axially. In other embodiments, the prongs may be angled (for example, by 10-20 degrees) toward the axis of the needle thereby increasing their effectiveness. This angulation is balanced to the need for efficient aspiration versus requirements for cutting. FIG. 3A shows an embodiment in which needle 20 and the prongs 26 extend coaxially with no bend in the needle or the prongs. In the embodiment of FIG. 3B, the needle includes bend 22 and the prongs 26 are angled radially inwardly. In FIG. 3C the prongs 26 are angled radially inwardly as discussed above, but the needle has no band.

The multiplicity of needle prongs may have various degrees of arc and length to the longitudinal perspective from the hand-piece. As cut from a tubular device the needle prongs, as described, would be partial elements of the classic circumferential phacoemulsification needle (consider a half pipe as the minimal design resulting in two needle prongs). Additionally the needle-prongs could be bent to varying degrees according to the inherent power described by that advantage.

The following are approximate dimensions of the various elements discussed.

Needle 18 may have a circular or ovoid cross-section at its tip 24 would vary from 0.8 mm to 1.5 mm.

The ID of tube 40 is approximately 0.5 to 0.9 mm.

The aperture 30 has a diameter of about 0.65 mm to 1.4 mm.

The OD of the sleeve 42 is in the range of 1.4 mm to 1.8 mm.

In a flared tip design the OD of a circle defined by the prongs 26 is approximately 0.95 mm.

The prongs 26 would vary from approximately 0.2 mm to 1.0 mm in length.

The plume formed by the irrigation fluid as it exits from the irrigation apertures is disposed at an angle of at least 90 degrees with the axis of the tube 40, and preferably greater than 90 degrees.

The silicone sleeve is drawn down along the shaft of the hand-piece stopping with a tight seal above the needle prongs and positioned in such a way as to provide the most efficient maintenance of the anterior chamber without setting up undue turbulence in relation to nuclear lens material at the lumen of the needle prong arrangement.

Figure 4:
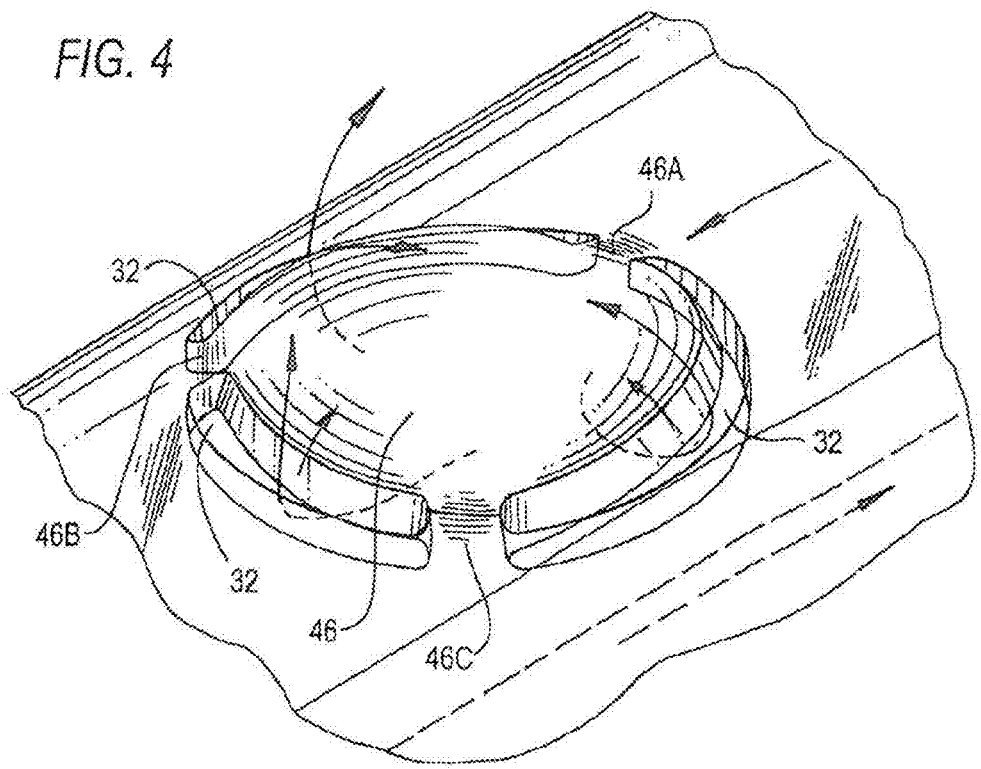
FIG. 4 shows an orthogonal view of an irrigation aperture with a flap constructed in accordance with this invention.

In a preferred embodiment, the irrigation apertures 32 through which fluid is expelled into the anterior chamber are provided with deflecting, collapsible flaps acting as the baffles 46 set along the silicone sleeve as shown in FIG. 4. Each flap includes a central portion 46C connected at one point with a hinge 46B to an edge of irrigating aperture 32, and one or more leashes 46A that are either very flexible and expand when fluid pressure is applied to the portion 46C to allow the portion 46C to separate from the aperture 32, or are connected only to main portion 46C and are provided to position the main portion 46C properly within the aperture 32. In this latter configuration, the central portion is biased toward the aperture 32 by the hinge 46B.

When infusion fluid is directed down the sleeve 42 surrounding the tube 40, the flaps 46 are made to inflate outward or otherwise open as a clam-like design while still partially fixed by hinge 46B. Further the flaps may be partially leashed proximally to the proximal edges of the port at the sleeve (more than one leash may be considered depending on the port size) in order to limit the excursion of the flap. Importantly, when no infusion fluid is provided, the flaps are folded along the sleeve 42 to act as a ramp to smooth insertion or removal of the instrument through the corneal or scleral wound. When fluid is not actively flowing in a vigorous manner, the flap will be collapsed or partially collapsed facilitating removal of the hand-piece from the eye. Aiding in the directing infusion flow a circumferential hub of thickened silicone just at the margin of distal port position would act to abruptly redirect fluid flow towards the ports.

In one embodiment, foot-pedal (not shown) coupled to the hand piece 10, can be placed in one of several positions (a standard arrangements for a generic phacoemulsification device) fluid flowing is initiated with some degree of force opens the flap to a prescribed degree allowing deflected fluid to flow across the capsular bag relatively lateral to the port.

The flap may have a central portion that is round, ovoid or some other distinguishable shape of silicone or some other flexible material continuous at both the hinge and leash across the distal and proximal edges of the edges of the irrigation apertures respectively which may be round or oval (or variously shaped) along the silicone sleeve just proximal to the metallic phacoemulsification tip 24. The 42 sleeve is tightly fit at its distal end, preventing or limiting fluid flow directly across the tip which would otherwise be directed into the posterior chamber.

The outer diameters of the irrigation apertures may be variously sized (e.g. 1.5-2 mm) in association with the intended rate of flow into the chambers of the eye.

Figure 5:
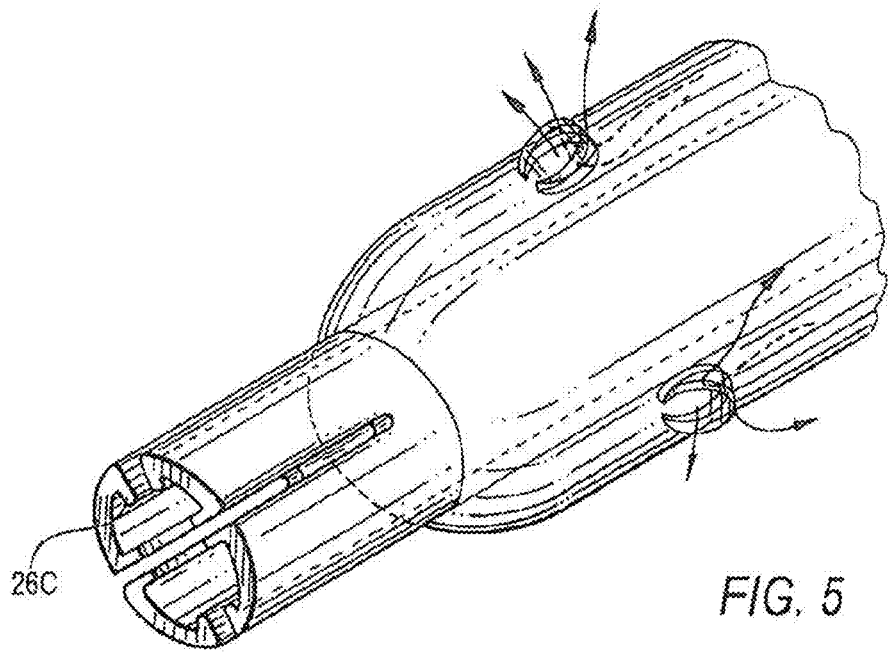
FIG. 5 shows an orthogonal view of another embodiment of the invention.

As previously mentioned, the tongs 26 can be created from a tube by making longitudinal cuts. The corners of the prongs can be rounded as illustrated in FIG. 5.

FIG. 6A shows a partial, somewhat diagrammatic view of the tip of an apparatus for performing phacoemulsification. The end prongs have been omitted for the sake of clarity. The tip includes a needle 40 and a somewhat flexible sleeve 42. As previously described, a fluid 44 is injected into the sleeve, it flows around the needle 40 and is ejected through apertures 30. Preferably, several apertures 30 are provided around the sleeve 40, preferably with flaps (not shown) for directing the fluid flow outside the sleeve in a predetermined direction or shape, as indicated by arrows A.

The present inventor has found that during the operation of the device, needle 40 does not stay in a concentric position, equidistant from the sleeve 42, but instead it deflects in one direction or another. Moreover, during the procedure, the deflection may change, so that, referring to FIG. 6B, the needle 40 can be deflected downwardly within, the sleeve, sideways, upward, or in any other random direction. This deflection may be a result of the surgeon moving his hand or wrist during the procedure due to the fulcrum defined at the corneal or scleral entry wound. As a result, some of the apertures (for example, aperture 30B in FIG. 6B can be either partially or fully occluded by the needle 40. As a result, the fluid flow from this aperture 30B, indicated by arrow B may be very weak or even-nonexistent while the fluid flow C through aperture 30A may be much stronger than the normal flow A in FIG. 6A. The reduced flow of arrow B is not very desirable because it produces in an imbalance in the flow of the fluid. The stronger fluid flow C is even more undesirable because it may cause the iris to flap around and move unpredictably (potentially damaging iris and blood vessels). It also forces the lens detritus and infused fluid to run forcefully to the edges of the crystalline lens and through lens zonules and into the back of the eye (vitreous cavity).

In order to solve this problem, in one embodiment shown in FIGS. 6C and 6D, stabilizers 53 are provided on the inner walls of the sleeve 42 as shown. The stabilizers 53 are disposed at axially spaced intervals along the sleeve 42. The positioning, numbers, and height of the stents/stabilizers is determined by the constituency of the sleeve material, its thickness, diameter, and length along the needle that it encases. For example, in FIG. 6D four stabilizers 53 are shown, spaced at about 90 degrees around the central needle 40. In one embodiment, the stabilizers have the same size and shape. In another embodiment, some of the stabilizers may be larger than others. As can be seen in FIG. 6D, the stabilizers need not come in permanent contact with the needle so that they will not interfere with its vibration. Preferably, the stabilizers are sized and shaped so that they do not block a significant portion of the annular space between the sleeve and the needle, and hence do not interfere with the fluid flowing therein. In one embodiment, they may be placed near the apertures and direct the fluid flow toward the apertures thereby reducing turbulence in the sleeve.

The purpose of the stabilizers is to prevent the needle 40 from deflecting by a large angle and therefore prevent the needle 40 from occulting any of the apertures (ports) 30.

In an alternate embodiment of the invention, the stabilizers 53 are disposed on, or attached to the outer wall of the needle 40 rather than the inner wall of the sleeve 42.

Obviously numerous modifications may be made to this invention without departing from its scope as defined in the appended claims.

I claim:

1. An apparatus for performing eye surgery comprising: a vibration mechanism; a handle connected to a source of irrigation fluid and including a needle having a cylindrical outside surface with a uniform needle diameter and a distal tip and being coupled to said vibration mechanism and adapted to be vibrated by said vibration mechanism, said handle further including an irrigation sleeve disposed around said needle and being configured for placement in the eye through a corneal or scleral wound; said sleeve having an inlet and a port near said distal tip and an inner surface having a cylindrical shape and extending between said inlet and said port and defining a cannula between said sleeve and said needle, said sleeve receiving said irrigation fluid through said inlet and conducting said irrigation fluid along said outside surface through said cannula to said port; and a plurality of stabilizers formed integrally with said sleeve between said inlet and extending inwardly into said cannula, said stabilizers being arranged within the sleeve to stabilize said needle and prevent said needle from deflection toward said irrigation aperture during said vibration; and wherein said stabilizers each have axial and circumferential dimensions smaller than the dimensions of the sleeve selected to prevent the stabilizer from blocking a significant portion of the cannula and interfere with the irrigation fluid flow.

2. The apparatus of claim 1 wherein said port is configured to generate a plume of irrigation fluid at an angle of at least 90 degrees with respect to a longitudinal axis of said needle.

3. The apparatus of claim 2 wherein said angle is over 90 degrees.

4. The apparatus of claim 1 wherein said tip includes an aspiration aperture disposed at said tip, said irrigation aperture and said port cooperating to generate an irrigation plume between said port and said aspiration aperture and away from said tip.

5. The apparatus of claim 4 wherein said sleeve is formed with a plurality of ports disposed around said needle, said ports cooperating with said aspiration aperture to shape said plume into a toroidal shape.

6. The apparatus of claim 1 wherein said tip includes a plurality of prongs.

7. A device associated with an apparatus with a vibrating mechanism for providing surgery in the outside or within capsular bag of an eye, said apparatus comprising: an elongated cylindrical tube terminating at one end with a tip and being adapted to couple to the apparatus at another end and adapted to vibrate, said tip having a cylindrical tip outer surface with a uniform diameter; a sleeve covering a portion of said tip and including with an inlet receiving irrigation fluid and an irrigation aperture arranged to expel irrigation fluid from said sleeve away from said tip, said sleeve having a cylindrical inner surface forming a cannula with said tip outer surface, said cannula conducting irrigation fluid from said inlet to said irrigation aperture; and a plurality of stabilizers disposed between said inlet and said aperture and arranged to stabilize said cylindrical tube during operation and prevent said cylindrical tube from occluding said irrigation aperture; and wherein said stabilizers each have axial and circumferential dimensions smaller than the dimensions of the sleeve inner surface selected to prevent the stabilizer from blocking a significant portion of the cannula and interfere with the irrigation fluid flow.

8. The device of claim 7 wherein said aperture is configured to generate a plume at an angle of at least 90 degrees with respect to a longitudinal axis of said needle.

9. The device of claim 7 wherein said tip is vibrating in a sonic frequency range.

10. The device of claim 7 wherein said tip is vibrating at a supersonic frequency range.

11. The device of claim 7 wherein said stabilizers are attached to said cylindrical inner surface.

12. The device of claim 7 wherein said stabilizers are attached to said tip outer surface.

* * * * *